United States Patent
Somberg et al.

(10) Patent No.: US 8,563,574 B2
(45) Date of Patent: Oct. 22, 2013

(54) PARENTERAL FORMULATION OF CLOPIDOGREL

(75) Inventors: John C. Somberg, Lake Forest, IL (US); Vasant V. Ranade, Lake Bluff, IL (US)

(73) Assignee: Academic Pharmaceuticals, Inc.

( * ) Notice: Subject to any disclaimer, the term of this patent is extended or adjusted under 35 U.S.C. 154(b) by 102 days.

(21) Appl. No.: 12/961,671

(22) Filed: Dec. 7, 2010

(65) Prior Publication Data

US 2012/0004256 A1    Jan. 5, 2012

Related U.S. Application Data

(60) Provisional application No. 61/267,198, filed on Dec. 7, 2009.

(51) Int. Cl.
| | | |
|---|---|---|
| *A01N 43/42* | (2006.01) | |
| *A61K 31/44* | (2006.01) | |
| *C07D 513/02* | (2006.01) | |
| *C07D 515/02* | (2006.01) | |

(52) U.S. Cl.
USPC .......................................... 514/300; 546/114

(58) Field of Classification Search
None
See application file for complete search history.

(56) References Cited

U.S. PATENT DOCUMENTS

| | | |
|---|---|---|
| 5,576,328 A | 11/1996 | Herbert et al. |
| 5,989,578 A | 11/1999 | Bernat et al. |
| 6,153,252 A | 11/2000 | Hossainy et al. |
| 6,383,471 B1 * | 5/2002 | Chen et al. .................... 424/45 |
| 6,667,299 B1 | 12/2003 | Ahlem et al. |
| 6,761,903 B2 | 7/2004 | Chen et al. |
| 7,148,211 B2 | 12/2006 | Mazess et al. |
| 7,183,272 B2 | 2/2007 | Aronhime et al. |
| 7,923,447 B2 | 4/2011 | Somberg et al. |
| 2006/0171948 A1 | 8/2006 | Weinstein et al. |

FOREIGN PATENT DOCUMENTS

| | | | |
|---|---|---|---|
| WO | WO 0010534 A1 * | 3/2000 | |
| WO | 2008134600 A1 | 11/2008 | |
| WO | WO 2008134600 A1 * | 11/2008 | |

OTHER PUBLICATIONS

Strickely, Robert G., Solubilizing Excipients in Oral and Injectable Formulations, Pharmaceutical Research 2004, 12(2), 201-229.
International Search Report and Written Opinion for PCT/US10/59194 (corresponding international filing), mailing date Jan. 30, 2012.

* cited by examiner

*Primary Examiner* — Jeffrey S. Lundgren
*Assistant Examiner* — Michael Schmitt
(74) *Attorney, Agent, or Firm* — Vance Intellectual Property PC

(57) ABSTRACT

Described herein are ways to solubilize clopidogrel for parenteral administration containing clopidogrel and a diluent NNDMA (N,N-dimethylacetamide); useful in the prevention of platelet aggregation in acute coronary syndrome, acute myocardial infarction or to prevent platelet facilitated thrombosis following coronary angioplasty and/or coronary stenting.

22 Claims, No Drawings

PARENTERAL FORMULATION OF CLOPIDOGREL

CROSS-REFERENCE TO RELATED APPLICATIONS

The present application claims priority benefit under 35 U.S.C. §119(e) of U.S. Provisional Patent Application Ser. No. 61/267,198 filed Dec. 7, 2009. The disclosure this application is incorporated herein by reference.

FIELD OF THE INVENTION

This invention relates to parenteral formulations of clopidogrel, a very insoluble anti-platelet agent.

BACKGROUND OF THE INVENTION

Many lipophilic anti-platelet agents such as clopidogrel are only sparingly or negligibly water-soluble. The poor water-solubility of these agents often results in major difficulties in formulation, particularly when intravenous solutions are needed. A number of approaches for preparing intravenous compositions of sparingly or poorly water-soluble drugs are available. These methods include: physio-chemical solubilization techniques such as micellar solubilization by means of surface-active agents, formation of complexes, solid solutions and solid dispersions by means of the use of suitable polymers; use of various co-solvent systems; and use of the formation of complexes by the addition of chelating agents such as citric acid, tartaric acid, amino acids, thioglycolic acid, and edetate sodium. Other approaches are the use of buffering agents such as acetate, citrate, glutamate and phosphate salts. However, buffers and chelating agents have been implicated in adverse effects such as nephrotoxicity and renal tubular necrosis. Each of these methods has its inherent limitations and the solubility levels that can be achieved with the methods discussed above are still insufficient to make their use in intravenous commercial products.

U.S. Pat. No. 7,148,211 describes parenteral formulation of several representative therapeutic agents including anti-platelet agents such as clopidogrel. It is described in U.S. Pat. No. '211 how a parenteral formulation can be prepared with the lipophilic drug clopidogrel, a non-ionic solubilizer polysorbate 20 present at a concentration of about 0.05% to about 5% with or without the lipophilic antioxidant butylated hydroxytoluene (BHT) present at a concentration of about 20 to about 2000 ppm. Additionally ethanol can be present at a concentration of 0 to 30% with or without an aqueous vehicle.

In another example, Acusphere has described their Imagify® technology that uses perfluorobutane polymer microspheres for dissolving water-insoluble drugs such as clopidogrel.

Sanofi-Aventis atents U.S. Pat. No. 5,576,328 and U.S. Pat. No. 5,989,578 describe the use of parenteral preparations of clopidogrel and a pharmaceutically acceptable acid addition salt together with a pharmaceutically acceptable carrier.

For parenteral, intranasal, or intramuscular administrations, aqueous suspensions and isotonic and injectable solutions are used that contain dispersing agents and/or wetting agents that are pharmacologically compatible (e.g., propylene glycol or butylene glycol). The active ingredient is provided in the form of a complex with cyclodextrin, (e.g., α, β, or gamma cyclodextrin or 2-hydroxypropyl-β-cyclodextrin).

US Patent Publication 2006/0171948 by Regeneron Pharmaceuticals describes administration by subcutaneous or IV injection or infusion of antiplatelet agents such as clopidogrel. This patent publication describes the use of microspheres for sterile filling and using a technology from CyDex Corporation that employes cyclodextrin and captisol for solubilization.

There still is a need for pharmaceutical formulations of lipophilic anti-platelet agents such as clopidogrel that overcome the limitations of the above described approaches.

SUMMARY OF THE INVENTION

In an aspect, the present invention provides a novel clopidogrel formulation that can be sterilized using filtration or heat and that is acceptable for intravenous administration to man.

In another aspect, the present invention provides a novel process for preparing a formulation of solubilized clopidogrel.

These and other aspects, which will become apparent during the following detailed description, have been achieved by the inventors' discovery that NNMDA (N,N-dimethylacetamide) can be useful in solubilizing clopidogrel.

DETAILED DESCRIPTION OF THE INVENTION

Intravenous formulations of clopidogrel in parenterally acceptable solvents are useful for the treatment of emergency ischemic conditions such as acutely developing myocardial infarction, acute coronary syndrome (ACS), or when coronary angioplasty and/or coronary stenting is to be undertaken. It can be beneficial for IV formulations of clopidogrel in parenterally acceptable solvents to be stable and remain clear and colorless for a period of at least one year before use.

Selection of NNDMA (N,N-dimethylacetamide, also referred to as DMA) over other solvents such as DMF, which belongs to structurally related groups of chemicals was based on the favorable physico-chemical characteristics of NNDMA, and it being an acceptable diluent for administration to man. Attempts were made to prepare parenteral solutions comprising clopidogrel at a concentration of 7.5-10 mg/mL in a number of buffers (pH 4-5) (see Table 1). These preparations resulted in insoluble clopidogrel being present in each case.

It was then attempted to dissolve clopidogrel in mixtures containing $D_5W$ (5% dextrose in water), propanol, isopropanol, propyleneglycol, polyethyleneglycol (PEG) 300, and PEG 400. Attempts to dissolve clopidogrel only in PEG did not result in clear solutions. Use of mixtures of PEG and propanol resulted in the formation of turbid solutions. Use of $D_5W$ to solubilize clopidogrel resulted in insoluble material being present. Addition of glycerol, Tween 80, Tween 40, DMSO, or polyvinyl pyrrolidone or applying heat did not improve solubility. However, formulations using PEG 300 and propyleneglocol combined with NNDMA were clear and clopidogrel was completely soluble, even when prepared at room temperature. The results of these experiments are described in Table 2.

Thus, in an aspect, the present invention provides a parenteral formulation, comprising:
  clopidogrel;
  1-50 wt. % NNDMA; and,
  remainder at least one parentally acceptable co-solvent.

In another embodiment, the present invention provides a parenteral formulation, comprising:
  clopidogrel;
  1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 6, 7, 8, 9, 10, 15, 20, 25, 30, 35, 40, 45, to 50% by volume NNDMA;

18, 19, 20, 21, 22, 23, 24, 25, 26, 27, 28, 29, 30, 31, 32, 33, 34, 35, 36, 3, 38, 39, 40, 41, 42, 43, 44, 45, 46, 47, 48, 49, 50, 51, 52, 53, 54, 55, 56, 57, 58, 59, 60, to 61% by volume propylene glycol; and, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, to 81% by volume PEG-300.

In another aspect, the present invention provides a parenteral formulation, wherein the pH of the formulation is from 4.5, 5, 5.5, 6.0, to 6.5. Additional examples of the pH include (a) 5.0, (b) 5.5, and (c) 6.0.

In another aspect, the present invention provides a parenteral formulation, wherein 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, to 150 mg/mL of clopidogrel is present in the formulation. Further examples of the concentration of clopidogrel include 7.5 mg/mL and 15 mg/mL.

Examples of the co-solvents include (a) 60% by volume propylene glycol and 38% by volume PEG-300, (b) 50% by volume propylene glycol and 48% by volume PEG-300, (c) 33% by volume propylene glycol and 65% by volume PEG-300, (d) 18% by volume propylene glycol and 80% by volume PEG-300, and (e) 20% by volume propylene glycol and 60% by volume PEG-300.

Additional examples of the amount of NNDMA present in the formulation include (a) 1-5% by volume, (b) 1.5-2.5% by volume, and (c) 2% by volume.

In another aspect, the present invention provides a parenteral formulation, comprising:
7.5 to 15 mg/mL clopidogrel;
1.5-2.5% by volume NNDMA (N,N-dimethylacetamide);
18-61% by volume propylene glycol; and,
38-81% by volume PEG-300.

In another aspect, the present invention provides a parenteral formulation, comprising:
7.5 mg/mL clopidogrel; and,
2% by volume NNDMA (N,N-dimethylacetamide).

In another aspect, the present invention provides a parenteral formulation, comprising:
15 mg/mL clopidogrel; and,
2% by volume NNDMA (N,N-dimethylacetamide).

In another aspect, the present invention provides a parenteral formulation, comprising:
7.5 to 15 mg/mL clopidogrel;
1.5-2.5% by volume NNDMA (N,N-dimethylacetamide);
18-61% by volume propylene glycol; and,
38-81% by volume PEG-300;
wherein the formulation has a pH of from 4.5-6.5.

In another aspect, the present invention provides a parenteral formulation, comprising:
7.5 mg/mL clopidogrel; and,
2% by volume NNDMA (N,N-dimethylacetamide);
wherein the formulation has a pH of from 4.5-6.5.

In another aspect, the present invention provides a parenteral formulation, comprising:
15 mg/mL clopidogrel; and,
2% by volume NNDMA (N,N-dimethylacetamide);
wherein the formulation has a pH of from 4.5-6.5.

In another aspect, the present invention provides a method of treating emergency ischemic conditions, comprising: administering a therapeutically effective amount of a formulation of the present invention to a patient in need thereof. Examples of emergency ischemic conditions include acutely developing myocardial infarction and acute coronary syndrome (ACS).

In another aspect, the present invention provides a method of treating a patient undergoing coronary angioplasty and/or coronary stenting, comprising: administering a therapeutically effective amount of a formulation of the present invention to a patient in need thereof is to be undertaken.

Clopidogrel as used herein refers to clopidogrel bisulfate.

All references cited herein are hereby incorporated in their entirety herein by reference.

Other features of the invention will become apparent in the course of the following descriptions of exemplary embodiments that are given for illustration of the invention and are not intended to be limiting thereof.

EXAMPLES

TABLE 1

Dissolution of Clopidogrel in Different Buffers

| Buffers | Buffer Concentration | |
|---|---|---|
| | 0.05M | 0.1M |
| Bis-Tris[1] | not soluble | not soluble |
| Bis-Tris[1] with 44 mg β-CD | " | " |
| Bis-Tris[1] with 66 mg β-CD | " | " |
| Bis-Tris[1] with 88 mg β-CD | " | " |
| Bis-Tris[1] with 176 mg β-CD | " | " |
| Bis-Tris[1] with 440 mg β-CD | " | " |
| CAPS[2] | " | " |
| CAPS[2] with 44 mg β-CD | " | " |
| CAPS[2] with 66 mg β-CD | " | " |
| CAPS[2] with 88 mg β-CD | " | " |
| CAPS[2] with 176 mg β-CD | " | " |
| CAPS[2] with 440 mg β-CD | " | " |
| TAPS[3] | " | " |
| TAPS[3] with 44 mg β-CD | " | " |
| TAPS[3] with 66 mg β-CD | " | " |
| TAPS[3] with 88 mg β-CD | " | " |
| TAPS[3] with 176 mg β-CD | " | " |
| TAPS[3] with 440 mg β-CD | " | " |
| HEPES[4] | " | " |
| HEPES[4] with 44 mg β-CD | " | " |
| HEPES[4] with 66 mg β-CD | " | " |
| HEPES[4] with 88 mg β-CD | " | " |
| HEPES[4] with 176 mg β-CD | " | " |
| HEPES[4] with 440 mg β-CD | " | " |
| AMPSO[5] | " | " |
| AMPSO[5] with 44 mg β-CD | " | " |
| AMPSO[5] with 66 mg β-CD | " | " |
| AMPSO[5] with 88 mg β-CD | " | " |
| AMPSO[5] with 176 mg β-CD | " | " |
| AMPSO[5] with 440 mg β-CD | " | " |
| Tricine[6] | " | " |
| Tricine[6] with 44 mg β-CD | " | " |
| Tricine[6] with 66 mg β-CD | " | " |
| Tricine[6] with 88 mg β-CD | " | " |
| Tricine[6] with 176 mg β-CD | " | " |
| Tricine[6] with 440 mg β-CD | " | " |
| Bicine[7] | " | " |
| Bicine[7] with 44 mg β-CD | " | " |
| Bicine[7] with 66 mg β-CD | " | " |
| Bicine[7] with 88 mg β-CD | " | " |
| Bicine[7] with 176 mg β-CD | " | " |
| Bicine[7] with 440 mg β-CD | " | " |
| TEA[8] | " | " |
| TEA[8] with 44 mg β-CD | " | " |
| TEA[8] with 66 mg β-CD | " | " |

TABLE 1-continued

Dissolution of Clopidogrel in Different Buffers

| Buffers | Buffer Concentration | |
|---|---|---|
| | 0.05M | 0.1M |
| TEA[8] with 88 mg β-CD | " | " |
| TEA[8] with 176 mg β-CD | " | " |
| TEA[8] with 440 mg β-CD | " | " |
| CHES[9] | " | " |
| CHES[9] with 44 mg β-CD | " | " |
| CHES[9] with 66 mg β-CD | " | " |
| CHES[9] with 88 mg β-CD | " | " |
| CHES[9] with 176 mg β-CD | " | " |
| CHES[9] with 440 mg β-CD | " | " |
| Saline | " | " |
| Saline with 44 mg β-CD | " | " |
| Saline with 66 mg β-CD | " | " |
| Saline with 88 mg β-CD | " | " |
| Saline with 176 mg β-CD | " | " |
| Saline with 440 mg β-CD | " | " |
| $D_5W$ | " | " |
| $D_5W$ with 44 mg β-CD | " | " |
| $D_5W$ with 66 mg β-CD | " | " |
| $D_5W$ with 88 mg β-CD | " | " |
| $D_5W$ with 176 mg β-CD | " | " |
| $D_5W$ with 440 mg β-CD | " | " |
| Na-Acetate pH 3.8 | " | " |
| Na-Acetate pH 3.8 with 44 mg β-CD | " | " |
| Na-Acetate pH 3.8 with 66 mg β-CD | " | " |
| Na-Acetate pH 3.8 with 88 mg β-CD | " | " |
| Na-Acetate pH 3.8 with 176 mg β-CD | " | " |
| Na-Acetate pH 3.8 with 440 mg β-CD | " | " |
| Na-Citrate pH 3.8 | " | " |
| Na-Citrate pH 3.8 with 44 mg β-CD | " | " |
| Na-Citrate pH 3.8 with 66 mg β-CD | " | " |
| Na-Citrate pH 3.8 with 88 mg β-CD | " | " |
| Na-Citrate pH 3.8 with 176 mg β-CD | " | " |
| Na-Citrate pH 3.8 with 440 mg β-CD | " | " |
| K-Phosphate pH 3.8 | " | " |
| K-Phosphate pH 3.8 with 44 mg β-CD | " | " |
| K-Phosphate pH 3.8 with 66 mg β-CD | " | " |
| K-Phosphate pH 3.8 with 88 mg β-CD | " | " |
| K-Phosphate pH 3.8 with 176 mg β-CD | " | " |
| K-Phosphate pH 3.8 with 440 mg β-CD | " | " |

[1] 2-Bis(2-Hydroxyethyl)amino-2(hydroxymethyl)-1,3-propanedol.
[2] 3-(cyclohexylamino)propane sulfonic acid.
[3] 3-([tris-hydroxymethyl)methyl]amino)propansulfonic acid.
[4] 2-(hydroxyethyl)-1-piperazine-ethane sulfonic acid.
[5] 3-[(1,1-dimethyl-2-hhydroxyethyl)amino]-2-hydroxypropane sulfonic acid.
[6] N-Tris (hydroxymethyl)methylglycine.
[7] N,N-Bis(2-hydroxyethyl)glycine.
[8] Triethanolamine.
[9] 2-(cyclohexylamine)ethane sulfonic acid.

Example 1

To 75 mg of clopidogrel, 0.2 mL of N,N-dimethylacetamide is added and the mixture is stirred gently till a clear solution is obtained. To this then 6.5 mL of PEG is added, that is followed by addition of 3.3 mL of propyleneglycol. The resulting solution is stirred gently, pH is adjusted to 4.5 to 6.5 with 0.1 N NaOH solution as needed, and then filtered through a 0.45 μm Millipore filter or 0.22 Millipore filter to obtain a clear colorless solution. Concentration of the clopidogrel is 7.5 mg/mL. Concentration of the NNDMA is 2% by volume.

Example 2

To 75 mg of clopidogrel, 0.2 mL of N,N-dimethylacetamide is added, and the mixture is stirred gently till a clear solution is obtained. To this then 8 mL of PEG 300 and 1.8 mL propyleneglycol are added. The resulting solution is stirred gently, pH is adjusted to 6 to 7.5 as needed, and then filtered though a 0.45 μm or 0.22 Millipore filter to obtain a clear colorless solution. Concentration of the clopidogrel is 7.5 mg/mL. Concentration of the NNDMA is 2% by volume.

Example 3

To 75 mg of clopidogrel, 0.2 mL of N,N-dimethylacetamide is added and the mixture is stirred gently till a clear solution is obtained. To this 0.8 mL of PEG 300 is added, the solution is stirred, a clear solution is obtained, and pH adjusted to be between 4.0 and 5.5, yielding a final volume of 1 mL. The solution is then filtered though a 0.45 μm or 0.22 Millipore filter to obtain a clear solution. Concentration of the clopidogrel is 75 mg/mL. Concentration of the NNDMA is 20% by volume.

Example 4

To 75 mg of clopidogrel, 0.2 mL of N,N-dimethylacetamide is added and then a mixture is stirred gently till a clear solution is obtained. To the solution 0.6 mL of PEG 300 is added. The mixture is a stable clear solution on stirring. To increase solubility and fluidity of the solution, 0.2 mL of propyleneglycol is added. The solution stirred and pH adjusted to 5.0 to 6.5 with 0.1 N NaOH solution. The material is then filtered through a 0.45μ or 0.22 Millipore filter and the solution remains clear and stable. Following this procedure, concentration of clopidogrel can be increased to 150 mg/mL.

Example 5

A solution of 150 mg of clopidogrel in 0.4 mL NNDMA and 0.6 mL of propyleneglycol (pH adjusted to 6.0) was made. This solution is then filtered through 0.45 μm or 0.22 Millipore filter and a clear solution remains.

TABLE 2

Dissolution of Clopidogrel in Solvents Containing NNDMA*

| Ex. | Clopidogrel (mg) | Solvent | Co-Solvent | pH | Result |
|---|---|---|---|---|---|
| 1. | 75 | PEG 300, 3.8 mL | Propyleneglycol 6 mL | 6.0 | clear |
| 2. | 75 | PEG 300, 4.8 mL | Propyleneglycol 5 mL | 5.5-6 | clear |
| 3. | 75 | PEG 300, 6.5 mL | Propyleneglycol 3.3 mL | 6.0 | clear |
| 4. | 75 | PEG 300, 8 mL | Propyleneglycol 1.8 mL | 6.0 | clear |
| 5. | 150** | PEG 300, 0.6 mL | Propyleneglycol 0.2 mL | 5.5 | clear |
| 6. | 75 | PEG 300, 0.6 mL | Propyleneglycol 0.2 mL | 5.5 | clear |
| 7. | 75 | PEG 300, 9.8 mL | None | 6.0 | not soluble |
| 8. | 75 | Propylene glycol, 9.8 mL | None | 6.0 | soluble |
| 9. | 75 | PEG 300, 9.8 mL | None | 5.5 | not clear (poor fluidity) |

TABLE 2-continued

Dissolution of Clopidogrel in Solvents Containing NNDMA*

| Ex. | Clopidogrel (mg) | Solvent | Co-Solvent | pH | Result |
|---|---|---|---|---|---|
| 10. | 75 | Propyleneglycol, 0.8 mL** | None | 5.5 | clear |
| 11. | 75 | Propyleneglycol, 4.8 mL | $D_5W$ 5 mL | 5.0 | cloudy |
| 12. | 75 | PEG, 4.8 mL | $D_5W$ 5 mL | 5.0 | not soluble |
| 13. | 75 | $D_5W$, 9.8 mL | None | 5.0 | not soluble |

*All examples are 10 mL and contain approximately 1.8% NNDMA by weight or 2% by volume, unless otherwise stated.
**Volume = 1 mL.

TABLE 3

Clopidogrel Stability after 12 Months at Room Temperature in Various Solvents Containing 1.8% NNDMA (0.2 ml)*

| Ex. | Clopidogrel (mg) | Solvent | Co-Solvent | pH | Stability |
|---|---|---|---|---|---|
| 1. | 75 | PEG 300, 3.8 mL | Propyleneglycol, 6 mL | 6.0 | clear, >99%** |
| 2. | 75 | PEG 300, 4.8 mL | Propyleneglycol, 5 mL | 5.5-6 | clear, >99% |
| 3. | 75 | PEG 300, 6.5 mL | Propyleneglycol, 3.3 mL | 6.0 | clear, >99% |
| 4. | 75 | PEG 300, 8 mL | Propyleneglycol, 1.8 mL | 6.0 | clear, >99% |
| 5. | 150*** | PEG 300, 0.6 mL | Propyleneglycol, 0.2 mL | 5.5 | clear, >99% |
| 6. | 75*** | PEG 300, 0.6 mL | Propyleneglycol, 0.2 mL | 5.5 | clear, >98% |

*All examples are 10 mL (volume) and contain approximately 1.8% NNDMA by weight or 2% by volume.
**Purity as determined by HPLC.
***Volume = 1 mL.

Numerous modifications and variations of the present invention are possible in light of the above teachings. It is therefore to be understood that within the scope of the appended claims, the invention may be practiced otherwise that as specifically described herein.

What is claimed is:

1. A parenteral formulation, comprising;
   a) clopidogrel;
   b) 1-50% by volume NNDMA (N,N-dimethylacetamide);
   c) 18-61% by volume propylene glycol; and,
   d) 38-81% by volume PEG-300.

2. The parenteral formulation of claim 1, wherein 1.0 mg/mL to 150 mg/mL of clopidogrel is present in the formulation.

3. The parenteral formulation of claim 1, wherein 7.5 mg/mL of clopidogrel is present in the formulation.

4. The parenteral formulation of claim 1, wherein 15 mg/mL of clopidogrel is present in the formulation.

5. The parenteral formulation of claim 1, wherein 60% by volume propylene glycol and 38% by volume PEG-300 is present in the formulation.

6. The parenteral formulation of claim 1, wherein 50% by volume propylene glycol and 48% by volume PEG-300 is present in the formulation.

7. The parenteral formulation of claim 1, wherein 33% by volume propylene glycol and 65% by volume PEG-300 is present in the formulation.

8. The parenteral formulation of claim 1, wherein 18% by volume propylene glycol and 80% by volume PEG-300 is present in the formulation.

9. The parenteral formulation of claim 1, wherein 20% by volume propylene glycol and 60% by volume PEG-300 is present in the formulation.

10. The parenteral formulation of claim 1, wherein 1-5% by volume NNDMA is present in the formulation.

11. The parenteral formulation of claim 1, wherein 1.5-2.5% by volume NNDMA is present in the formulation.

12. The parenteral formulation of claim 1, wherein 2% by volume NNDMA is present in the formulation.

13. The parenteral formulation of claim 1, wherein the pH of the formulation is from 4.5 to 6.5.

14. The parenteral formulation of claim 1, wherein the pH of the formulation is 5.0.

15. The parenteral formulation of claim 1, wherein the pH of the formulation is 5.5.

16. The parenteral formulation of claim 1, wherein the pH of the formulation is 6.0.

17. The parenteral formulation of claim 1, comprising:
   a) 7.5 to 15 mg/mL clopidogrel;
   b) 1.5-2.5% by volume NNDMA (N,N-dimethylacetamide);
   c) 18-61% by volume propylene glycol; and,
   d) 38-81% by volume PEG-300.

18. The parenteral formulation of claim 17, comprising:
   a) 7.5 mg/mL clopidogrel; and,
   b) 2% by volume NNDMA (N,N-dimethylacetamide).

19. The parenteral formulation of claim 17, comprising:
   a) 15 mg/mL clopidogrel; and,
   b) 2% by volume NNDMA (N,N-dimethylacetamide).

20. The parenteral formulation of claim 17, wherein the formulation has a pH of from 4.5-6.5.

21. The parenteral formulation of claim 17, comprising:
   a) 7.5 mg/mL clopidogrel; and,
   b) 2% by volume NNDMA (N,N-dimethylacetamide);
   wherein the formulation has a pH of from 4.5-6.5.

22. The parenteral formulation of claim 17, comprising:
   a) 15 mg/mL clopidogrel; and,
   B) 2% by volume NNDMA (N,N-dimethylacetamide);
   wherein the formulation has a pH of from 4.5-6.5.

* * * * *